(12) United States Patent
Drysdale

(10) Patent No.: US 9,145,356 B2
(45) Date of Patent: *Sep. 29, 2015

(54) PERFLUOROPOLYVINYL MODIFIED ARYL INTERMEDIATES AND MONOMERS

(71) Applicant: E I DU PONT DE NEMOURS AND COMPANY, Wilmington, DE (US)

(72) Inventor: Neville Everton Drysdale, Newark, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/068,535

(22) Filed: Oct. 31, 2013

(65) Prior Publication Data

US 2014/0135518 A1 May 15, 2014

Related U.S. Application Data

(60) Provisional application No. 61/726,260, filed on Nov. 14, 2012.

(51) Int. Cl.

| | |
|---|---|
| C07C 235/48 | (2006.01) |
| C07C 59/68 | (2006.01) |
| C07C 43/23 | (2006.01) |
| C07C 47/575 | (2006.01) |
| C07C 49/84 | (2006.01) |
| C07C 65/21 | (2006.01) |
| C07C 41/06 | (2006.01) |
| C07C 43/205 | (2006.01) |
| C07C 67/31 | (2006.01) |
| C07C 69/92 | (2006.01) |
| C07C 41/48 | (2006.01) |
| C07C 43/313 | (2006.01) |
| C07C 43/315 | (2006.01) |
| C07C 45/64 | (2006.01) |

(52) U.S. Cl.
CPC ............... *C07C 235/48* (2013.01); *C07C 41/06* (2013.01); *C07C 41/48* (2013.01); *C07C 43/205* (2013.01); *C07C 43/23* (2013.01); *C07C 43/313* (2013.01); *C07C 43/315* (2013.01); *C07C 45/64* (2013.01); *C07C 47/575* (2013.01); *C07C 49/84* (2013.01); *C07C 65/21* (2013.01); *C07C 67/31* (2013.01); *C07C 69/92* (2013.01)

(58) Field of Classification Search
CPC .............................. C07C 59/68; C07C 235/48
USPC ......................................... 560/62; 568/442
See application file for complete search history.

(56) References Cited

U.S. PATENT DOCUMENTS

| | | | |
|---|---|---|---|
| 4,460,791 | A | 7/1984 | Cooke |
| 4,577,036 | A | 3/1986 | Falk |
| 4,876,018 | A | 10/1989 | Karydas |
| 5,198,570 | A | 3/1993 | Feiring |
| 5,643,495 | A | 7/1997 | Bartmann et al. |
| 5,646,222 | A | 7/1997 | Maekawa et al. |
| 7,531,700 | B2 | 5/2009 | Petrov |
| 2006/0006364 | A1 | 1/2006 | Shundo et al. |
| 2007/0134440 | A1 | 6/2007 | Kato |
| 2011/0001088 | A1 | 1/2011 | Ootsuki et al. |
| 2012/0277460 | A1 | 11/2012 | Percec et al. |

FOREIGN PATENT DOCUMENTS

| | | |
|---|---|---|
| DE | 3828063 A1 | 2/1990 |
| DE | 4015681 A1 | 11/1991 |
| DE | 4015681 C2 | 11/1991 |
| EP | 0295813 A2 | 12/1988 |
| EP | 0355025 A2 | 8/1989 |
| EP | 0355025 A3 | 8/1989 |
| EP | 355025 A1 * | 2/1990 |
| EP | 0391390 A1 | 10/1990 |
| EP | 0391390 B1 | 10/1990 |

(Continued)

OTHER PUBLICATIONS

Dlouha, Journal of Fluorine Chemistry, 220, 117, 149-159.*
Machine translation for the EP 355025 document.*
U.S. Appl. No. 14/068,603, filed Oct. 31, 2013, Drysdale.
U.S. Appl. No. 14/068,784, filed Oct. 31, 2013, Drysdale.
U.S. Appl. No. 14/068,930, filed Oct. 31, 2013, Drysdale.
Search Report and Written Opinion, PCT/2013/069020 Dated Jan. 20, 2014.
Search Report and Written Opinion, PCT/2013/069029 Dated Jan. 7, 2014.
Search Report and Written Opinion, PCT/2013/069031 Dated Jan. 14, 2014.
Search Report and Written Opinion, PCT/2014/062643 Dated Dec. 12, 2014.
Furin, G. et al. "Reaction of 1,1,2-trifluoro-2-hexaflouro-2'-(heptafluoropropoxy-propoxyethylene with amines or alcohols", Journal of Fluorine Chemistry, 106, (2000), pp. 13-14, XP002718135.

(Continued)

*Primary Examiner* — Yong Chu
*Assistant Examiner* — Ana Z Muresan

(57) ABSTRACT

A compound of formula (I)

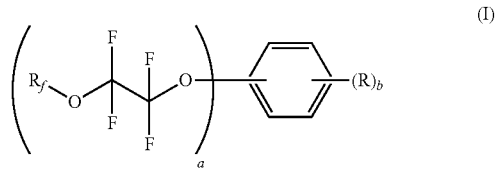

wherein $R_f$ is —$CF_3$, —$C_2F_5$, or —$CF_2CFXCF_3$; X is —F, or —$OC_3F_7$; Y is —H, —Cl, or —Br; R is —OH, —(OCH$_2$CH$_2$)$_m$OH, —(CH$_2$)$_n$(OCH$_2$CH$_2$)$_m$OH, —O—C(O)—R$^1$, —(CH$_2$)$_n$O—C(O)R$^1$, —(OCH$_2$CH$_2$)$_m$OC(O)—R$^1$, —C(O)NH$_w$(CH$_2$CH$_2$OH)$_{2-w}$, —C≡N, —C≡CH; n is 1 to 10; m is 1 to 10; R$^1$ is C$_1$ to C$_{10}$ alkyl; a is 1 to 5; b is 1 to 5; and w is 0, 1 or 2.

11 Claims, No Drawings

(56) References Cited

FOREIGN PATENT DOCUMENTS

| EP | 0610861 | A1 | 8/1994 |
|---|---|---|---|
| EP | 0638629 | A2 | 2/1995 |
| EP | 0638629 | A3 | 2/1995 |
| EP | 0638629 | B1 | 2/1995 |
| EP | 1036790 | A1 | 9/2000 |
| EP | 1411104 | A1 | 4/2004 |
| EP | 1411104 | B1 | 5/2007 |
| GB | 1376315 | A | 12/1974 |
| GB | 1404351 | A | 8/1975 |
| GB | 2245587 | A | 1/1992 |
| JP | 04159272 | | 6/1992 |
| JP | 1994172266 | A | 6/1994 |
| JP | 1997255608 | A | 9/1997 |
| JP | 2006117564 | A | 5/2006 |
| JP | 2006137856 | A | 6/2006 |
| JP | 2011148761 | A | 8/2011 |
| WO | 2007/149449 | A2 | 12/2007 |
| WO | 2007/149449 | A3 | 12/2007 |

OTHER PUBLICATIONS

Dlouha, Ivine, Reactivity Study of 1,1,2,4,4,5,7,7,8,8,9,9,9-tridecafluoro-5-trifluoromethyl-3,6-dioxanon-1-ene in nucleophilic 6 reactions: fluorination properties of secondary amine adducts, Journal of Fluorine Chemistry, 117, (2002), pp. 149-159.

* cited by examiner

1 …

PERFLUOROPOLYVINYL MODIFIED ARYL INTERMEDIATES AND MONOMERS

FIELD OF THE INVENTION

The present invention comprises aryl compounds having partially fluorinated tails which can be useful as intermediates and starting materials for producing various water and oil repellents, soil resists, and surfactants.

BACKGROUND OF THE INVENTION

Water and oil repellents, soil resists, and surfactants compounds generally are prepared from linear perfluorinated alcohols. These alcohols are expensive and are prepared through several step synthesis. These alcohols are either then reacted to make final products or further synthesized into intermediates prior to making final products. New starting materials are needed that do not utilize linear perfluorinated alcohols.

U.S. Pat. No. 7,531,700 teaches fluorinated solvents having benzene rings with a) perfluorinated pendent alkyl groups, b) alkyl, alkoxy, or oxyalkyl groups and c) optionally halogen pendent groups useful for the manufacture of organic electronic devices. These solvents are non-reactive.

Patent Application WO 2007/149449 teaches fluoroalkoxystyrenes prepared by contacting fluorinated olefin with a solution of hydroxystyrene. These fluoroalkoxystyrenes are useful in resins, elastomers, polymers or coatings.

What is needed are nonlinear compounds as starting materials and intermediates to produce compounds for water and oil repellents, soil resists, and surfactants compounds. The present invention meets this need.

SUMMARY OF THE INVENTION

The present invention comprises a compound of formula (I)

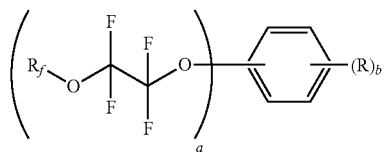

(I)

wherein
$R_f$ is $-CF_3$, $-C_2F_5$, $-CF_2CFXCF_3$;
X is $-F$, or $-OC_3F_7$;
Y is $-H$, $-Cl$, or $-Br$;
R is $-OH$, $-(CH_2)_nOH$, $-(OCH_2CH_2)_mOH$, $-(CH_2)_n(OCH_2CH_2)_mOH$, $-O-C(O)-R^1$, $-(CH_2)_nO-C(O)R^1$, $-(OCH_2CH_2)_mOC(O)-R^1$, $-C(O)NH_w(CH_2CH_2OH)_{2-w}$, $-C\equiv N$, $-C\equiv CH$, or $-C(O)R^2$;
n is 1 to 10;
m is 1 to 10;
$R^1$ is $C_1$ to $C_{10}$ alkyl;
$R^2$ is $-H$, $C_1$ to $C_{10}$ alkyl, $-Cl$, or $-OCH_2CH_2OH$;
a is 1 to 5;
b is 1 to 5;
and w is 0, 1 or 2.

The present invention also comprises a method of producing compounds of Formula (XX)

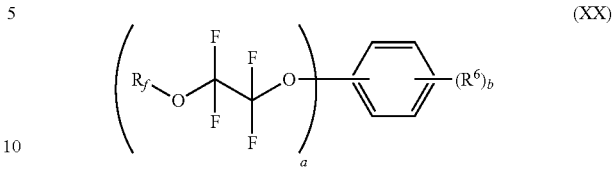

(XX)

wherein
$R_f$ is $-CF_3$, $-C_2F_5$, or $-CF_2CFXCF_3$;
X is $-F$, or $-OC_3F_7$;
Y is $-H$, $-Cl$, or $-Br$;
$R^6$ is $-OH$, $-(CH_2)_nOH$, $-(OCH_2CH_2)_mOH$, $-O-C(O)-R^1$, $-(CH_2)_nO-C(O)-R^1$, $-(OCH_2CH_2)_mOC(O)R^1$; $-C(O)NH_w(CH_2CH_2OH)_{2-w}$, $-C\equiv N$, $-C\equiv CH$, $-NO_2$, $-C(O)R^2$, or $-C(O)-OR^4$; $-CH=CH_2$;
n is 1 to 10;
m is 1 to 10;
$R^1$ is $C_1$ to $C_{10}$ alkyl;
$R^2$ is $-H$, $C_1$ to $C_{10}$ alkyl, $-Cl$, or $-OCH_2CH_2OH$; $R^3$ is H or $CH_3$;
$R^4$ is $-H$, or $C_1$ to $C_{10}$ alkyl;
a is 1 to 5;
b is 1 to 5;
and w is 0, 1 or 2;
comprising contacting a compound of Formula (XXI)

(XXI)

wherein
$R^7$ is $-OH$, $-(CH_2)_nOH$, $-(OCH_2CH_2)_mOH$, $-(CH_2)_n(OCH_2CH_2)_mOH$, $-O-C(O)-R^1$, $-(CH_2)_nO-C(O)-R^1$, $-(OCH_2CH_2)_mOC(O)-R^1$; $-C(O)NH_w(CH_2CH_2OH)_{2-w}$, $-C\equiv N$, $-C\equiv CH$, $-NO_2$, $-C(O)R^2$, $-C(O)-OR^4$, or $-CH=CH_2$;
n is 1 to 10;
m is 1 to 10;
$R^1$ is $C_1$ to $C_{10}$ alkyl;
$R^2$ is $-H$, $C_1$ to $C_{10}$ alkyl, $-Cl$, or $-OCH_2CH_2OH$;
$R^4$ is $-H$, or $C_1$ to $C_{10}$ alkyl;
a is 1 to 5;
b is 1 to 5;
with one or more compounds of formula (XIV)

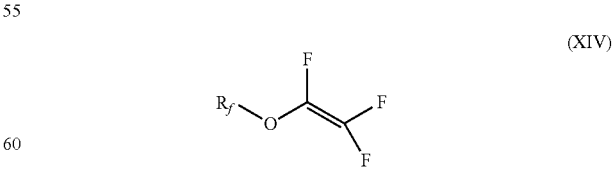

(XIV)

wherein
$R_f$ is $-CF_3$, $-C_2F_5$, or $-CF_2CFXCF_3$;
X is $-F$, or $-OC_3F_7$; and
Y is $-H$, $-Cl$, or $-Br$
in the presence of a base and a solvent.

DETAILED DESCRIPTION

Herein trademarks are shown in upper case.
The present invention provides a compound of formula (I)

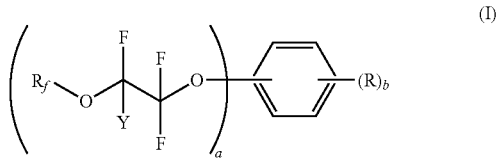
(I)

wherein
$R_f$ is —$CF_3$, —$C_2F_5$, or —$CF_2CFXCF_3$;
X is —F, or —$OC_3F_7$;
Y is —H, —Cl, or —Br;
R is —OH, —$(CH_2)_nOH$, —$(OCH_2CH_2)_mOH$, —$(CH_2)_n(OCH_2CH_2)_mOH$, —O—C(O)—$R^1$, —$(CH_2)_nO$—C(O)$R^1$, —$(OCH_2CH_2)_mOC(O)$—$R^1$; —$C(O)NH_w(CH_2CH_2OH)_{2-w}$, —C≡N, —C≡CH, or —C(O)$R^2$;
  n is 1 to 10;
  m is 1 to 10;
  $R^1$ is $C_1$ to $C_{10}$ alkyl;
  $R^2$ is —H, $C_1$ to $C_{10}$ alkyl, —Cl, or —$OCH_2CH_2OH$;
  $R^3$ is H or $CH_3$;
  a is 1 to 5;
  b is 1 to 5; and
  w is 0, 1 or 2.

Compounds of the present invention include pendent groups $(R_f$—O—CFY—$CF_2O$—$)_a$ and $(R)_b$ and wherein a is 1 to 5 and b is 1 to 5. Compounds of the present invention may have 1, 2, 3, 4 or 5 pendent groups of $R_f$—O—CFY—$CF_2O$—, and 1, 2, 3, 4, or 5 pendent groups of —R, and mixtures thereof, provided that the total number of pendent groups is less than or equal to 6. The $R_f$—O—CFY—$CF_2O$— and —R groups may be ortho, para, or meta on the benzene ring or combinations thereof.

Preferred compounds of Formula (I) include those wherein R is —OH, —$(CH_2)_nOH$, —$(OCH_2CH_2)_mOH$, and —$(CH_2)_n(OCH_2CH_2)_mOH$, wherein each of m and n are independently 1, 2, 3, 4, 5, or 6. More preferred are compounds of Formula (I) wherein R is —OH, —$(CH_2)_nOH$, —$(OCH_2CH_2)_mOH$, and —$(CH_2)_n(OCH_2CH_2)_mOH$, wherein each of m and n are independently 1, 2, or 3. Also preferred are those wherein $R_f$ is —$CF_3$ or —$C_2F_5$, and R is —OH, $(CH_2)_nOH$, —$(OCH_2CH_2)_mOH$, and —$(CH_2)_n(OCH_2CH_2)_mOH$, wherein each of m and n are independently 1, 2, or 3.

Additional preferred compounds of Formula (I) are those wherein R is —O—C(O)—$R^1$ or —C(O)$R^2$, wherein $R^1$ is an alkyl of 1, 2, 3, 4, 5, or 6 carbons; and $R^2$ is H or an alkyl of 1, 2, 3, 4, 5, or 6 carbons. More preferred are compounds of Formula (I) wherein R is —O—C(O)—$R^1$ or —C(O)$R^2$, wherein $R^1$ is an alkyl of 1, 2, or 3 carbons; and $R^2$ is H or an alkyl of 1, 2, or 3 carbons. Also preferred are those wherein $R_f$ is —$CF_3$ or —$C_2F_5$, and R is —O—C(O)—$R^1$ or —C(O)$R^2$, wherein $R^1$ is an alkyl of 1, 2, or 3 carbons; and $R^2$ is H or an alkyl of 1, 2, or 3 carbons.

Also preferred are compounds of Formula (I) wherein R is —C≡N, or —C≡CH. More preferred are compounds of Formula (I) wherein R is —C≡N or —C≡CH, and $R_f$ is —$CF_3$ or —$C_2F_5$. Other preferred compounds of Formula (I) are those wherein R is —$C(O)NH_w(CH_2CH_2OH)_{2-w}$ wherein w is 0, 1 or 2. More preferred are compounds of Formula (I) wherein R is —$C(O)NH_w(CH_2CH_2OH)_{2-w}$ wherein w is 0, 1 or 2, and $R_f$ is —$CF_3$ or —$C_2F_5$.

Compounds of Formula (I) can be produced in various ways. Preferred specific examples of compounds of Formula (I) include, but are not limited to,

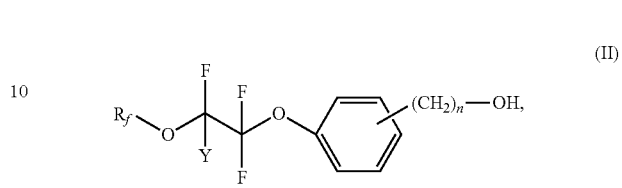
(II)

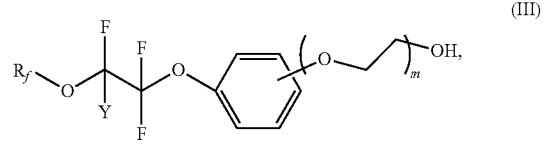
(III)

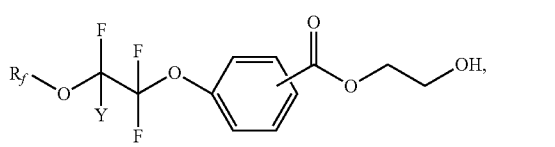
(IV)

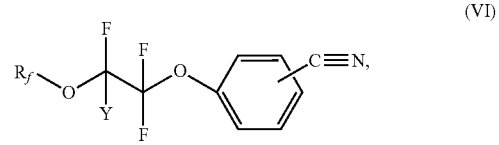
(VI)

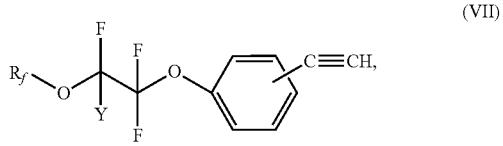
(VII)

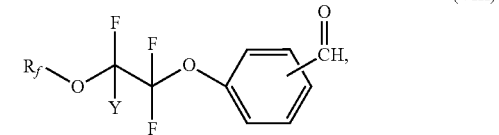
(VIII)

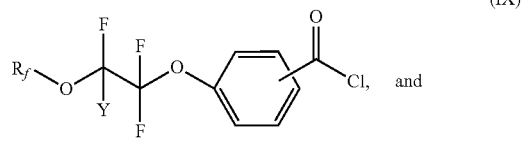
(IX)

and

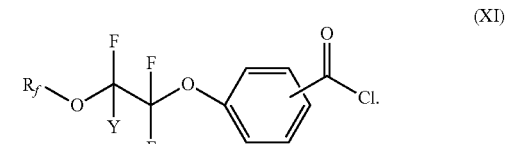
(XI)

In one embodiment, compounds of the present invention of Formula (I), wherein $R_f$ is —$CF_3$, —$C_2F_5$, —$CF_2CFXCF_3$; X is —F, or —$OC_3F_7$; Y is —H, —Cl, or —Br and R is —OH, —$(CH_2)_nOH$, —$(OCH_2CH_2)_mOH$, —C(O)—O—$R^1$, —$C(O)NH_2$, —C≡N, —C≡CH, or —C(O)$R^2$, can be prepared by contacting a variety of functionalized aryl rings of Formula (XIII)

wherein $R^5$ is —OH, —(CH$_2$)$_n$OH, —(OCH$_2$CH$_2$)$_m$OH, —(CH$_2$)$_n$(OCH$_2$CH$_2$)$_m$OH, —(CH$_2$)$_n$(OCH$_2$CH$_2$)$_m$OH, —O—C(O)—R$^1$, —C(O)NH$_2$, —C≡N, —C≡CH, or —C(O)R$^2$; n is 1 to 10; m is 1 to 10; R$^1$ is C$_1$ to C$_{10}$ alkyl; R$^2$ is —H, C$_1$ to C$_{10}$ alkyl, —Cl, or —OCH$_2$CH$_2$OH; a is 1 to 5; and b is 1 to 5 with one or more perfluorovinyl ethers of formula (XIV)

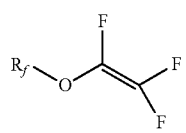

wherein R$_f$ is —CF$_3$, —C$_2$F$_5$, or —CF$_2$CFXCF$_3$; X is —F, or —OC$_3$F$_7$; and Y is —H, —Cl, or —Br.

For compounds of Formula (XIV), when R$_f$ is —CF$_3$, the compound is perfluoromethylvinyl ether of Formula (XV)

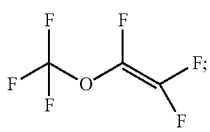

when R$_f$ is —C$_2$F$_5$, the compound is a perfluorovinyl ethyl ether of Formula (XVI)

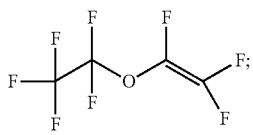

when R$_f$ is —CF$_2$CFXCF$_3$ and X is —F, the compound is a perfluoropropylvinyl ether of Formula (XVII)

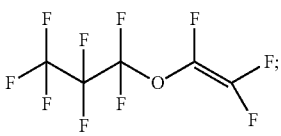

and when R$_f$ is —CF$_2$CFXCF$_3$ and X is —OC$_3$F$_7$, the compound is a perfluoropropylvinyl ether of Formula (XVIII)

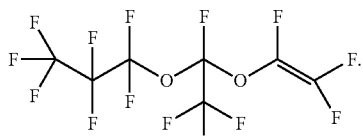

The reaction of the aryl compounds of Formula (XIII) with perfluorovinyl ethers of Formula (XIV) can be completed in a solvent and a base. Suitable bases include those known to deprotonate the hydrogen of a phenol. Examples of such bases include, but are not limited to, potassium carbonate, sodium carbonate, and potassium bicarbonate. Examples of such bases include, but are not limited to, potassium carbonate, sodium carbonate, and potassium bicarbonate. Examples of suitable solvents include, but are not limited to, tetrahydrofuran, carbon tetrachloride, and carbon tetrabromide. In Formula (I), when tetrahydrofuran is the solvent, then Y is —H. In Formula (I), when carbon tetrachloride is the solvent, then Y is —Cl. In Formula (I), when carbon tetrabromide is the solvent, then Y is —Br. The reaction temperature can be complete between room temperature and solvent reflux temperatures.

In one embodiment, the present invention relates to a compound of Formula (I), wherein R$_f$ is —CF$_3$, —C$_2$F$_5$, —CF$_2$CFXCF$_3$; X is —F, or —OC$_3$F$_7$; Y is —H, —Cl, or —Br and R is —OH, —(CH$_2$)$_n$OH, —(OCH$_2$CH$_2$)$_m$OH, or —(CH$_2$)$_n$(OCH$_2$CH$_2$)$_m$OH; n is 0 to 10; m is 1 to 10. Compounds of this embodiment can be prepared by reacting compounds of Formula (XIII) wherein R is —OH, —(CH$_2$)$_n$OH, —(OCH$_2$CH$_2$)$_m$OH, or —(CH$_2$)$_n$(OCH$_2$CH$_2$)$_m$OH; n is 1 to 10; m is 1 to 10 with one or more compounds of Formula (XIV) as defined above.

In a second embodiment, the present invention relates to a compound of Formula (I), wherein R$_f$ is —CF$_3$, —C$_2$F$_5$, —CF$_2$CFXCF$_3$; X is —F, or —OC$_3$F$_7$; and Y is —H, —Cl, or —Br and R is —C(O)—O—R$^1$; or —C(O)R$^2$; and n is 1 to 10; m is 1 to 10; R$^1$ is C$_1$ to C$_{10}$ alkyl; R$^2$ is —H, C$_1$ to C$_{10}$ alkyl, —Cl, or —OCH$_2$CH$_2$OH, and R$^4$ is —H, or C$_1$ to C$_{10}$ alkyl. Compounds of the second embodiment can be prepared by reacting compounds of Formula (XIII) wherein R is —C(O)—O—R$^1$; or —C(O)R$^2$; and n is 1 to 10; m is 1 to 10; R$^1$ is C$_1$ to C$_{10}$ alkyl; and R$^2$ is —H, C$_1$ to C$_{10}$ alkyl, —Cl, or —OCH$_2$CH$_2$OH; with one or more compounds of Formula (XIV) as defined above.

In a third embodiment, the present invention relates to a compound of Formula (I), wherein R$_f$ is —CF$_3$, —C$_2$F$_5$, or —CF$_2$CFXCF$_3$; X is —F, or —OC$_3$F$_7$; and Y is —H, —Cl, or —Br and R is —C≡N, or —C≡CH. Compounds of the third embodiment can be prepared by reacting compounds of Formula (XIII) wherein R is —C≡N, or —C≡CH, with one or more compounds of Formula (XIV), as defined above.

In a fourth embodiment, the present invention relates to alcohol amide containing compounds of Formula (I), wherein R$_f$ is —CF$_3$, —C$_2$F$_5$, or —CF$_2$CFXCF$_3$; X is —F, or —OC$_3$F$_7$; and Y is —H, —Cl, or —Br and R is —C(O)NH$_w$(CH$_2$CH$_2$OH)$_{2-w}$ wherein w is 0, 1 or 2. In this embodiment, the alcohol amide containing compounds of Formula (I) can be prepared by contacting a compound of Formula (I) wherein R$_f$ is —CF$_3$, —C$_2$F$_5$, —CF$_2$CFXCF$_3$; X is —F, or —OC$_3$F$_7$; and Y is —H, —Cl, or —Br and R is —C(O)R$^2$ and R$^2$ is —Cl, with ethanol amine (wherein w is 1) or di(ethanol) amine (wherein w is 0). Compounds of Formula (I) wherein R is —C(O)R$^2$ and R$^2$ is —Cl can be prepared by contacting compounds of Formula (I) wherein R is —C(O)OH with thionyl chloride. Compounds of Formula (I) wherein R is —C(O)OH can be prepared by contacting compounds of Formula (I) wherein R is —C(O)R$^2$ and R$^2$ is —OCH$_2$CH$_2$OH with potassium hydroxide. Compounds of Formula (I) wherein R is —C(O)R$^2$ and R$^2$ is —OCH$_2$CH$_2$OH can be prepared as defined above in the second embodiment.

Alternatively in this fourth embodiment, alcohol amide containing compounds of Formula (I) can be prepared by contacting N,N-diethanolphenol amide with a perfluorovinyl ether of Formula (XIII) in a solvent and a base, such as potassium carbonate.

In a fifth embodiment, the present invention relates to a method of producing compounds of Formula (XX)

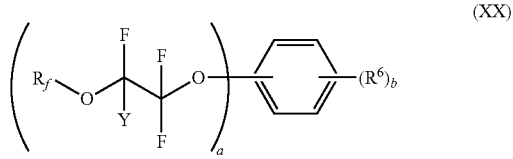

wherein
$R_f$ is —$CF_3$, —$C_2F_5$, or —$CF_2CFXCF_3$;
X is —F, or —$OC_3F_7$;
Y is —H, —Cl, or —Br;
$R^6$ is —OH, —$(CH_2)_nOH$, —$(OCH_2CH_2)_mOH$, —$(CH_2)_n(OCH_2CH_2)_mOH$, —O—C(O)—$R^1$, —$(CH_2)_nO$—C(O)—$R^1$, —$(OCH_2CH_2)_mOC(O)$—$R^1$; —$C(O)NH_w(CH_2CH_2OH)_{2-w}$, —C≡N, —C≡CH, —$NO_2$, —$C(O)R^2$, —$C(O)OR^4$; or —CH=$CH_2$;
n is 1 to 10;
m is 1 to 10;
$R^1$ is $C_1$ to $C_{10}$ alkyl;
$R^2$ is —H, $C_1$ to $C_{10}$ alkyl, —Cl, or —$OCH_2CH_2OH$;
$R^3$ is H or $CH_3$;
$R^4$ is —H, or $C_1$ to $C_{10}$ alkyl;
a is 1 to 5;
b is 1 to 5;
and w is 0, 1 or 2;
comprising contacting a compound of Formula (XXI)

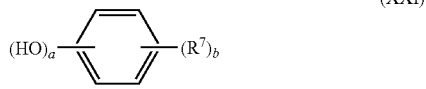

wherein $R^7$ is —$(CH_2)_nOH$, —$(OCH_2CH_2)_mOH$, —$(CH_2)_n(OCH_2CH_2)_mOH$, —O—C(O)—$R^1$, —$C(O)NH_w(CH_2CH_2OH)_{2-w}$, —C≡N, —C≡CH, —$NO_2$, —$C(O)R^2$, —C(O)—$OR^4$, or —CH=$CH_2$; n is 1 to 10; m is 1 to 10; $R^1$ is $C_1$ to $C_{10}$ alkyl; $R^2$ is —H, $C_1$ to $C_{10}$ alkyl, —Cl, or —$OCH_2CH_2OH$; $R^4$ is —H, or $C_1$ to $C_{10}$ alkyl; a is 1 to 5; b is 1 to 5; w is 0, 1, or 2 with one or more compounds of formula (XIV)

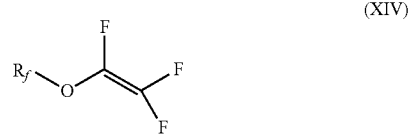

wherein $R_f$ is —$CF_3$, —$C_2F_5$, or —$CF_2CFXCF_3$; X is —F, or —$OC_3F_7$; and Y is —H, —Cl, or —Br in the presence a base and a solvent. Suitable bases include those known to deprotonate the hydrogen of a phenol. Examples of such bases include, but not limited to, potassium carbonate, sodium carbonate, and potassium bicarbonate. Examples of suitable solvents include, but not limited to, tetrahydrofuran, carbon tetrachloride, and carbon tetrabromide.

Compounds of the present invention and as defined above, are useful, for example, as starting monomers and intermediates for 1) the preparation of polyacrylate copolymers used for oil and water repellency, 2) as reactants for producing phosphate surfactants, and 3) in producing partially fluorinated urethanes useful for oil and water repellency as well as stain resistance to fibrous substrates. The compounds produced from the method of the present invention are not only useful as intermediates and starting materials for repellency compounds, but also include those compounds useful in the electronics displays, such as, for example, compounds of Formula (XX) wherein $R^7$ is —CH=$CH_2$.

EXAMPLES

Materials

Perfluorovinyl ethers 1,1,1,2,2,3,3-heptafluoro-3-((1,2,2-trifluorovinyl)oxy)propane and 1,1,1,2,2,3,3-heptafluoro-3-(1,1,1,2,3,3-hexafluoro-3-(1,2,2-trifluorovinyloxy)propan-2-yloxy)propane are commercially available from E. I. du Pont de Nemours and Company, Wilmington, Del. All other reactants, unless otherwise specified, are available from Sigma-Aldrich, St. Louis, Mo.

Example 1

(4-(1,1,2-trifluoro-2-(perfluoropropoxy)ethoxy)phenyl)methanol

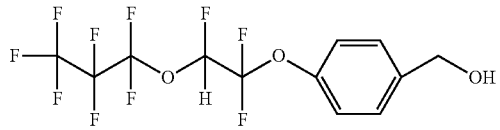 [SMILES: OCc1ccc(OC(F)(F)C(F)OC(F)(F)C(F)(F)C(F)(F)F)cc1]

In the dry box, tetrahydrofuran (2000 mL) and 4-(hydroxymethyl)phenol (24.8 g, 0.20 mol) were added to a round bottom flask equipped with a stirrer. Potassium carbonate (13.8 g, 0.10 mol) was then added to the flask. 1,1,1,2,2,3,3-heptafluoro-3-((1,2,2-trifluorovinyl)oxy)propane (79.89 g, 0.30 mol) was then added via the addition funnel and the reaction was placed in an oil bath and heated to a gentle reflux overnight. The content was analyzed by proton NMR to be (4-(1,1,2-trifluoro-2-(perfluoropropoxy)ethoxy)phenyl) methanol. The potassium carbonate was removed via filtration and the resulting material concentrated via roto-evaporation. Vacuum distillation afforded the desired material, bp 89-92° C. at 1.00 torr, 87.65 yield).

Example 2

(4-(1,1,2-trifluoro-2-(1,1,2,3,3,3-hexafluoro-2-(perfluoropropoxy)propoxy)ethoxy)phenyl)methanol

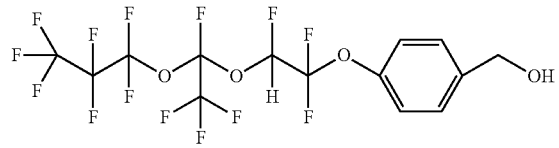 [SMILES: OCc1ccc(OC(F)(F)C(F)OC(F)(OC(F)(F)C(F)(F)C(F)(F)F)C(F)(F)F)cc1]

In the dry box, tetrahydrofuran (50 mL) and 4-(hydroxymethyl)phenol (0.62 g, 0.005 mol) were added to a round bottom flask equipped with a stirrer. Potassium carbonate (0.345 g, 0.0025 mol) was then added to the flask. 1,1,1,2,2,3,3-Heptafluoro-3-(1,1,1,2,3,3-hexafluoro-3-(1,2,2-trifluorovinyloxy)propan-2-yloxy)propane (3.24 g, 0.0075 mol) was then added via the addition funnel and the reaction was placed in an oil bath and heated to a gentle reflux over 2 days. The content was analyzed by proton NMR and shown to be (4-(1,1,2-trifluoro-2-(1,1,2,3,3,3-hexafluoro-2-(perfluoropropoxy)propoxy)ethoxy)phenyl)methanol.

Example 3

2-(2-(1,1,2-trifluoro-2-(perfluoropropoxy)ethoxy)phenoxy)ethanol

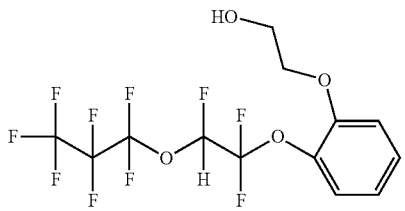 [SMILES: OCCOc1ccccc1OC(F)(F)C(F)OC(F)(F)C(F)(F)C(F)(F)F]

In the dry box, tetrahydrofuran (2000 mL) and 2-(hydroxyethoxy)phenol (30.8 g, 0.20 mol) were added to a round bottom flask equipped with a stirrer. Potassium carbonate (13.8 g, 0.10 mol) was then added to the flask. 1,1,1,2,2,3,3-heptafluoro-3-((1,2,2-trifluorovinyl)oxy)propane (79.89 g, 0.30 mol) was then added via the addition funnel and the reaction was placed in an oil bath and heated to a gentle reflux overnight. The content was analyzed by proton NMR to be 2-(2-(1,1,2-trifluoro-2-(perfluoropropoxy)ethoxy)phenoxy)ethanol. The potassium carbonate was removed via filtration and the resulting material concentrated via roto-evaporation. Vacuum distillation afforded the desired material, bp 96-97° C. at 1.0-1.2 torr, 94.86 yield).

Example 4

2-(2-(1,1,2-trifluoro-2-(1,1,2,3,3,3-hexafluoro-2-(perfluoropropoxy)propoxy)ethoxy)phenoxy)ethanol

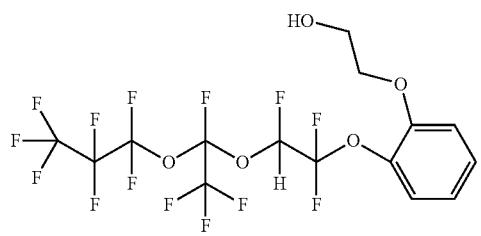 [SMILES: OCCOc1ccccc1OC(F)(F)C(F)OC(F)(OC(F)(F)C(F)(F)C(F)(F)F)C(F)(F)F]

In the dry box, tetrahydrofuran (50 mL) and 2-(hydroxyethoxy)phenol (0.77 g, 0.005 mol) were added to a round bottom flask equipped with a stirrer. Potassium carbonate (0.345 g, 0.0025 mol) was then added to the flask. 1,1,1,2,2,3,3-Heptafluoro-3-(1,1,1,2,3,3-hexafluoro-3-(1,2,2-trifluorovinyloxy)propan-2-yloxy)propane (3.24 g, 0.0075 mol) was then added via the addition funnel and the reaction was placed in an oil bath and heated to a gentle reflux overnight. The content was analyzed by proton NMR and shown to be 2-(2-(1,1,2-trifluoro-2-(1,1,2,3,3,3-hexafluoro-2-(perfluoropropoxy)propoxy)ethoxy)phenoxy)ethanol.

Example 5

2-hydroxyethyl 4-(1,1,2-trifluoro-2-(1,1,2,3,3,3-hexafluoro-2-(perfluoropropoxy)propoxy)ethoxy)benzoate

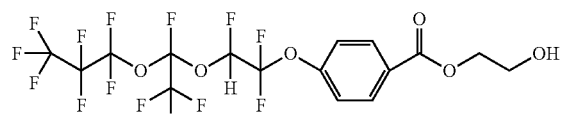

In the dry box, tetrahydrofuran (50 mL) and 2-hydroxyethyl 4-hydroxybenzoate (0.91 g, 0.005 mol) were added to a round bottom flask equipped with a stirrer. Potassium carbonate (0.345 g, 0.0025 mol) was then added to the flask. 1,1,1,2,2,3,3-Heptafluoro-3-(1,1,1,2,3,3-hexafluoro-3-(1,2,2-trifluorovinyloxy)propan-2-yloxy)propane (3.24 g, 0.0075 mol) was then added via the addition funnel and the reaction was placed in an oil bath and heated to a gentle reflux overnight. The content was analyzed by proton NMR and shown to be 2-hydroxyethyl 4-(1,1,2-trifluoro-2-(1,1,2,3,3,3-hexafluoro-2-(perfluoropropoxy)propoxy)ethoxy)benzoate.

Example 6

1-ethynyl-3-(1,1,2-trifluoro-2-(1,1,2,3,3,3-hexafluoro-2-(perfluoropropoxy)propoxy)ethoxy)benzene

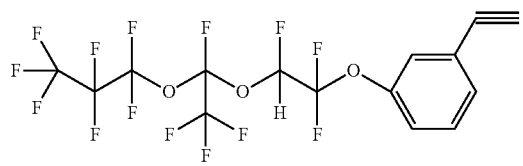

In the dry box, tetrahydrofuran (50 mL) and 3-ethynylphenol (0.59 g, 0.005 mol) were added to a round bottom flask equipped with a stirrer. Potassium carbonate (0.345 g, 0.0025 mol) was then added to the flask. 1,1,1,2,2,3,3-Heptafluoro-3-(1,1,1,2,3,3-hexafluoro-3-(1,2,2-trifluorovinyloxy)propan-2-yloxy)propane (3.24 g, 0.0075 mol) was then added via the addition funnel and the reaction was placed in an oil bath and heated to a gentle reflux overnight. The content was analyzed by proton NMR and shown to be 1-ethynyl-3-(1,1,2-trifluoro-2-(1,1,2,3,3,3-hexafluoro-2-(perfluoropropoxy)propoxy)ethoxy)benzene.

Example 7

4-(1,1,2-trifluoro-2-(1,1,2,3,3,3-hexafluoro-2-(perfluoropropoxy)propoxy)ethoxy)benzaldehyde

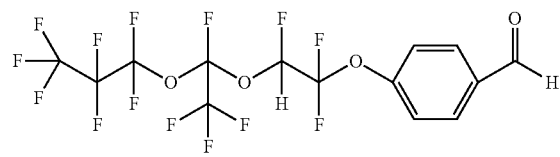 [SMILES: O=Cc1ccc(OC(F)(F)C(F)OC(F)(OC(F)(F)C(F)(F)C(F)(F)F)C(F)(F)F)cc1]

In the dry box, tetrahydrofuran (25 mL) and 4-hydroxybenzaldehyde (0.61 g, 0.005 mol) were added to a round bottom flask equipped with a stirrer. Potassium carbonate (0.175 g, 0.00126 mol) was then added to the flask. 1,1,1,2,2,3,3-Heptafluoro-3-(1,1,1,2,3,3-hexafluoro-3-(1,2,2-trifluorovinyloxy)propan-2-yloxy)propane (3.24 g, 0.0075 mol) was then added via the addition funnel and the reaction was placed in an oil bath and heated to a gentle reflux for two hours. The content was analyzed by proton NMR and shown to be 1-ethynyl-3-(1,1,2-trifluoro-2-(1,1,2,3,3,3-hexafluoro-2-(perfluoropropoxy)propoxy)ethoxy)benzene.

Example 8

1-(4-(1,1,2-trifluoro-2-(perfluoropropoxy)ethoxy)phenyl)ethanone

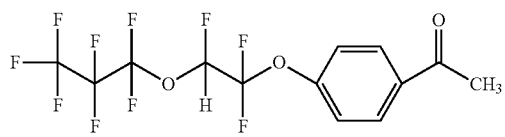 [SMILES: CC(=O)c1ccc(OC(F)(F)C(F)OC(F)(F)C(F)(F)C(F)(F)F)cc1]

In the dry box, tetrahydrofuran (50 mL) and 1-(4-hydroxyphenyl)ethanone (0.68 g, 0.005 mol) were added to a round bottom flask equipped with a stirrer. Potassium carbonate (0.175 g, 0.00126 mol) was then added to the flask. 1,1,1,2,2,3,3-heptafluoro-3-((1,2,2-trifluorovinyl)oxy)propane (1.99 g, 0.0075 mol) was then added via the addition funnel and the reaction was placed in an oil bath and heated to a gentle reflux for 5.5 hours. The content was analyzed by proton NMR and shown to be 1-ethynyl-3-(1,1,2-trifluoro-2-(1,1,2,3,3,3-hexafluoro-2-(perfluoropropoxy)propoxy)ethoxy)benzene.

Example 9

1-(4-(2-chloro-1,1,2-trifluoro-2-(perfluoropropoxy)ethoxy)phenyl)ethanone

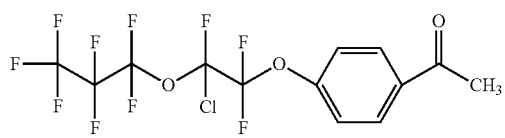 [SMILES: CC(=O)c1ccc(OC(F)(F)C(F)(Cl)OC(F)(F)C(F)(F)C(F)(F)F)cc1]

In the dry box, tetrahydrofuran (25 mL), dimethyl formamide (10.0 mL) and 1-(4-hydroxyphenyl)ethanone (0.68 g, 0.005 mol) were added to a round bottom flask equipped with a stirrer. Potassium carbonate (0.175 g, 0.00126 mol) was then added to the flask. 1,1,1,2,2,3,3-heptafluoro-3-((1,2,2-trifluorovinyl)oxy)propane (1.99 g, 0.0075 mol) was then added via the addition funnel and the reaction was placed in an oil bath and heated to a gentle reflux for six hours. The content was analyzed by proton NMR and shown to be 1-(4-(2-chloro-1,1,2-trifluoro-2-(perfluoropropoxy)ethoxy)phenyl)ethanone.

Example 10

1-(4-(1,1,2-trifluoro-2-(1,1,2,3,3,3-hexafluoro-2-(perfluoropropoxy)propoxy)ethoxy)phenyl)ethanone

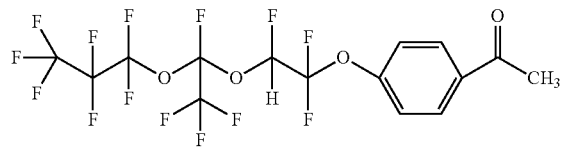 [SMILES: CC(=O)c1ccc(OC(F)(F)C(F)OC(F)(OC(F)(F)C(F)(F)C(F)(F)F)C(F)(F)F)cc1]

In the dry box, tetrahydrofuran (25 mL) and 1-(4-hydroxyphenyl)ethanone (0.68 g, 0.005 mol) were added to a round bottom flask equipped with a stirrer. Potassium carbonate (0.175 g, 0.00126 mol) was then added to the flask. 1,1,1,2,2,3,3-Heptafluoro-3-(1,1,1,2,3,3-hexafluoro-3-(1,2,2-trifluorovinyloxy)propan-2-yloxy)propane (3.24 g, 0.0075 mol) was then added via the addition funnel and the reaction was placed in an oil bath and heated to a gentle reflux for 5.5 hours. The content was analyzed by proton NMR and shown to be 1-(4-(1,1,2-trifluoro-2-(1,1,2,3,3,3-hexafluoro-2-(perfluoropropoxy)propoxy)ethoxy)phenyl)ethanone.

Example 11 methyl 4-(1,1,2-trifluoro-2-(1,1,2,3,3,3-hexafluoro-2-(perfluoropropoxy)propoxy)ethoxy)benzoate

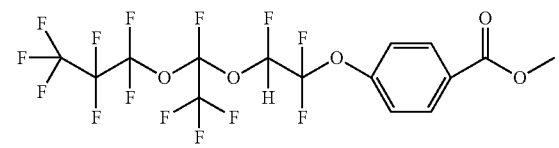 [SMILES: COC(=O)c1ccc(OC(F)(F)C(F)OC(F)(OC(F)(F)C(F)(F)C(F)(F)F)C(F)(F)F)cc1]

In the dry box, THF (500 mL) and methyl 4-hydroxybenzoate (26.6 g, 0.175 mol) were added to an oven dry RB flask equipped with a stirrer, Potassium carbonate (12.00 g, 0.087 mol) was then added. 1,1,1,2,2,3,3-Heptafluoro-3-(1,1,1,2,3,3-hexafluoro-3-(1,2,2-trifluorovinyloxy)propan-2-yloxy)propane (94.5 g, 0.219 mol) was then added via the addition funnel and the reaction allowed to stir at room temperature. The reaction mixture was heated to a gentle reflux, oil temperature about 80° C., under nitrogen overnight. An aliquot was withdrawn and concentrated under vacuum and analyzed via proton NMR that showed the complete conversion to the desired material. The cooled reaction mixture was then filtered through silica gel and then concentrated at reduced pressure, resulting in 101.52 g (99.33%) yield of the desired material.

Example 12

4-(1,1,2-trifluoro-2-(1,1,2,3,3,3-hexafluoro-2-(perfluoropropoxy)propoxy)ethoxy)benzoic acid

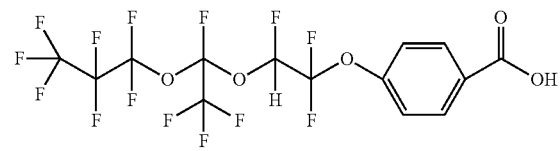 [SMILES: O=C(O)c1ccc(OC(F)(F)C(F)OC(F)(OC(F)(F)C(F)(F)C(F)(F)F)C(F)(F)F)cc1]

Water (500.0 mL) and potassium hydroxide were added to a round bottom flask equipped with a stirrer. Methyl 4-(1,1,2-trifluoro-2-(1,1,2,3,3,3-hexafluoro-2-(perfluoropropoxy)propoxy)ethoxy)benzoate (50.0 g, 0.0856 mol), as prepared in Example 11, was then added via the addition funnel and the reaction was placed in an oil bath and heated to a gentle reflux overnight. The flask was allowed to cool before acidifying with concentrated HCl, down to ph~1.0. The precipitate was filtered and dried overnight. The solids were analyzed by proton NMR to be 4-(1,1,2-trifluoro-2-(1,1,2,3,3,3-hexafluoro-2-(perfluoropropoxy)propoxy)ethoxy)benzoic acid.

Example 13

4-(1,1,2-trifluoro-2-(1,1,2,3,3,3-hexafluoro-2-(perfluoropropoxy)propoxy)ethoxy)benzoyl chloride

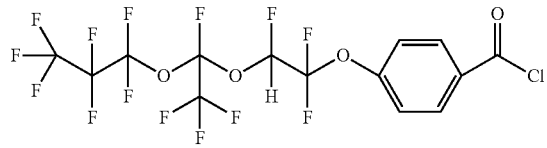 [SMILES: O=C(Cl)c1ccc(OC(F)(F)C(F)OC(F)(OC(F)(F)C(F)(F)C(F)(F)F)C(F)(F)F)cc1]

4-(1,1,2-trifluoro-2-(1,1,2,3,3,3-hexafluoro-2-(perfluoropropoxy)propoxy)ethoxy)benzoic acid (52.00 g, 0.0912 mol) as prepared in Example 12 and thionyl chloride (365 g, 3.09 mol) were place in an oven dried RB flask equipped with a stirrer, reflux condenser and under nitrogen. The reaction was placed in an oil bath and heated to a gentle reflux overnight. The content was analyzed by proton NMR and shown to be 4-(1,1,2-trifluoro-2-(1,1,2,3,3,3-hexafluoro-2-(perfluoropropoxy)propoxy)ethoxy)benzoyl chloride.

Example 14

N,N-bis(2-hydroxyethyl)-4-(1,1,2-trifluoro-2-(1,1,2,3,3,3-hexafluoro-2-(perfluoropropoxy)propoxy)ethoxy)benzamide

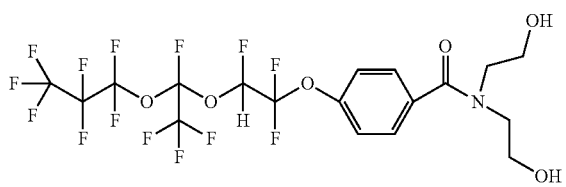 [SMILES: O=C(c1ccc(OC(F)(F)C(F)OC(F)(OC(F)(F)C(F)(F)C(F)(F)F)C(F)(F)F)cc1)N(CCO)CCO]

In the dry box, tetrahydrofuran (50 mL) and diethanol amine (0.714 g, 0.0068 mol) were added to a round bottom flask equipped with a stirrer. 4-(1,1,2-trifluoro-2-(1,1,2,3,3,3-hexafluoro-2-(perfluoropropoxy)propoxy)ethoxy)benzoyl chloride (2.00 g, 0.0034 mol) as prepared in Example 13 was then added and the reaction was stirred for one hour. The content was analyzed by proton NMR and shown to be N,N-bis(2-hydroxyethyl)-4-(1,1,2-trifluoro-2-(1,1,2,3,3,3-hexafluoro-2-(perfluoropropoxy)propoxy)ethoxy)benzamide.

Example 15

1-(1,1,2-trifluoro-2-(1,1,2,3,3,3-hexafluoro-2-(perfluoropropoxy)propoxy)ethoxy)-4-vinylbenzene

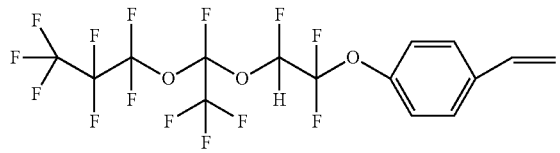 [SMILES: C=Cc1ccc(OC(F)(F)C(F)OC(F)(OC(F)(F)C(F)(F)C(F)(F)F)C(F)(F)F)cc1]

In the dry box, THF (50 mL) and 4-vinylphenol (5.00 g of a 10% solution in propylene glycol) were added to an oven dry RB flask equipped with a stirrer, Potassium carbonate (0.35 g, 0.0025 mol) was then added. 1,1,1,2,2,3,3-Heptafluoro-3-(1,1,1,2,3,3-hexafluoro-3-(1,2,2-trifluorovinyloxy)propan-2-yloxy)propane (2.70 g, 0.00625 mol) was then added via the addition funnel and the reaction allowed to stir at room temperature. The reaction mixture was heated to a gentle reflux under nitrogen overnight. An aliquot was withdrawn and concentrated under vacuum and analyzed via proton NMR which showed the complete conversion to be 1-(1,1,2-trifluoro-2-(1,1,2,3,3,3-hexafluoro-2-(perfluoropropoxy)propoxy)ethoxy)-4-vinylbenzene. The cooled reaction mixture was then concentrated at reduced pressure taken up in methylene chloride washed with water (~25 mL) separated, then dried over anhydrous sodium sulfate. The separated organic phase was then concentrated at reduced pressure and then column chromatograph on silica gel obtaining 1.15 g (about 50.0%) of the theoretical yield) of product.

What is claimed is:
1. A compound of formula (I)

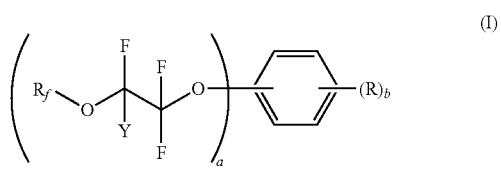

wherein
$R_f$ is —$CF_3$, —$C_2F_5$, or —$CF_2CFXCF_3$;
X is —F, or —$OC_3F_7$;
Y is —H, —Cl, or —Br;
R is —OH, —$(OCH_2CH_2)_mOH$, —$(CH_2)_n(OCH_2CH_2)_mOH$, —O—C(O)—$R^1$, —$(OCH_2CH_2)_mOC(O)$—$R^1$, —$C(O)NH_w(CH_2CH_2OH)_{2-w}$, —C≡N, or ≡C≡CH;
n is 1 to 10;
m is 1 to 10;
$R^1$ is $C_1$ to $C_{10}$ alkyl;
a is 1 to 5;
b is 1 to 5;
and w is 0, 1 or 2.
2. A compound of claim 1, wherein $R_f$ is —$CF_3$.
3. A compound of claim 1, wherein $R_f$ is —$C_2F_5$.

4. A compound of claim 1, wherein $R_f$ is $-CF_2CFXCF_3$ and X is $-F$.

5. A compound of claim 1, wherein $R_f$ is $-CF_2CFXCF_3$ and X is $-OC_3F_7$.

6. A compound of claim 1, wherein R is $-OH$, $-(OCH2CH2)mOH$, or $-(CH_2)_n(OCH_2CH_2)_mOH$.

7. A compound of claim 1, wherein R is $-C\equiv N$, $-C\equiv CH$, or $-NO_2$.

8. A compound of claim 1, wherein R is $-C(O)NH_w(CH_2CH_2OH)_{2-w}$ and w is 0, 1 or 2.

9. A compound of claim 1, wherein Y is H.

10. A compound of claim 1, wherein Y is Cl.

11. A compound of claim 1, wherein Y is Br.

* * * * *